United States Patent [19]

Stevens, Jr. et al.

[11] Patent Number: 4,659,670

[45] Date of Patent: Apr. 21, 1987

[54] BIOLOGICAL DESULFURIZATION OF COAL

[75] Inventors: Stanley E. Stevens, Jr.; Wilella D. Burgess, both of State College, Pa.

[73] Assignee: The Standard Oil Company

[21] Appl. No.: 495,657

[22] Filed: May 18, 1983

[51] Int. Cl.$^4$ .................... D06M 16/00; C12P 39/00; C12N 1/26; C10G 32/00

[52] U.S. Cl. .................. 435/262; 44/1 SR; 435/42; 435/172.1; 435/248; 435/253; 435/264; 435/281; 435/282; 435/822; 435/831; 435/850; 435/874

[58] Field of Search ............... 435/172.1, 42, 264, 435/281, 282, 248, 253, 831, 850, 262, 874, 822; 44/1 SR

[56] References Cited

U.S. PATENT DOCUMENTS

| | | | |
|---|---|---|---|
| 3,218,252 | 8/1963 | Glover et al. | 210/611 |
| 3,266,889 | 4/1964 | Duncan et al. | 435/262 |
| 3,305,353 | 3/1964 | Duncan et al. | 435/262 |
| 4,206,288 | 6/1980 | Detz et al. | 435/267 |

OTHER PUBLICATIONS

Kargi. Enzyme Microb. Technol., 1982 (Jan.), vol. 4, pp. 13–19.

*The Prokaryotes,* vol. 1, edited by M. P. Starr et al., 1981, pp. 1023–1036, The Genera *Thiobacillus* and *Thiomicrospira,* Kuenen et al.

Starkey "Ind. Eng. Chem." (1956) vol. 48, No. 9, pp. 1429–1437.

Microbiological Mining, Sci. Amer. 247(2): 44–53 (Aug. 1982).

Biotechnology News, vol. 2(6) Aug. 15, 1982.

*Primary Examiner*—Sidney Marantz
*Assistant Examiner*—Patricia Kate White
*Attorney, Agent, or Firm*—Bruce E. Harang; David J. Untener; Larry W. Evans

[57] ABSTRACT

A process for the preparation of microorganisms, ATCC No. 39327 which are capable of reproducible reduction of sulfur, particularly organic sulfur, in coal wherein the novel microorganisms are grown in situ enriched with sulfur compounds and subsequently grown in the presence of a coal substrate and nutrient medium while maintaining an essentially neutral pH. Contacting an aqueous coal slurry with the novel microorganism of the present invention provides coal having reduced organic sulfur content.

20 Claims, 7 Drawing Figures

BIOLOGICAL DESULFURIZATION OF COAL

BACKGROUND OF THE INVENTION

The present invention relates to a process for the preparation of microorganisms which are capable of reproducible reduction of sulfur in coal and, more particularly, to a process for the microbial desulfurization of coal.

An increasing awareness of the need to utilize alternative energy sources has prompted renewed interest in obtaining satisfactory methods of cleanly and efficiently burning coal. A substantial disadvantage long felt by the industry is the deleterious effect upon the environment which results from the products of coal combustion. Emission of sulfur oxides into the atmosphere has long been of particular concern.

The presence of sulfur in coal appears in three basic forms; as sulfates, pyrite and organic sulfur. Of the three, sulfates are the least significant, comprising less than 0.5 weight percent of the coal. Pyritic and organic sulfur, however, may each constitute as much as 3.5 weight percent of the coal or from 40 to 60% of the total sulfur content, respectively. Thus, it is apparent that removal of an effective portion of this sulfur content prior to coal combustion would substantially reduce the emission of sulfur oxides into the atmosphere.

Commercial attention has primarily been focused upon the removal of pyritic sulfur which has been relatively easy to facilitate. These processes include numerous physical and mechanical techniques such as heavy media separation, selective agglomeration, floatation, jigging, magnetic separation, leaching and hydrosulfurization. However, the removal of organic sulfur has not met with the same success. By organic sulfur, is meant, that sulfur which is chemically bound within the coal matrix. Organic sulfur is present in four major forms. These are mercaptans or thiols, sulfide, disulfide and aromatic ring sulfur as exemplified by the thiophene system. Since organic sulfur is chemically bound within the coal molecule, effective removal techniques employed must be essentially chemical or biological.

Processes for the biological removal of sulfur from coal are known in the art but again have only been successful for the oxidation of pyritic sulfur. For example, such a process is disclosed by U.S. Pat. No. 4,206,288 which employs an iron and sulfur oxidizing microorganism selected from the *Thiobacillus ferroxidans* group. Microorganisms chosen from this acidophilic group have long been known to have the capability of oxidizing the sulfide and ferrous iron in ores containing sulfide minerals. For example, U.S. Pat. No. 2,829,964 discloses a process for leaching metals such as copper from mixed oxide and sulfide copper ores utilizing an acid solution containing these bacteria.

Oxidation of the sulfide and/or ferrous iron to sulfate and ferric iron can be utilized to release numerous other metals from the mineral lattice. These include iron, nickel, zinc, molybdenum, copper, uranium and aluminum. Other processes which employ *Thiobacillus ferroxidans* for these known capabilities are disclosed, for example, in U.S. Pat. Nos. 3,218,252, 3,266,889 and 3,305,353. None of the aforementioned references, however, show any effect on the reduction of organic sulfur, although, as indicated, pyritic sulfur has been oxidized and thereby removed from coal with some success.

Methods for the removal of organic sulfur from coal are known but are quite expensive and particularly inefficient, usually employing extreme conditions such as high pressure and high temperature. Typically, the coal product treated by these processes is substantially altered and often may not be utilized for its intended purpose.

SUMMARY OF THE INVENTION

It is therefore one object of the present invention to provide a novel microorganism which is capable of reproducible sulfur metabolism.

Another object of this invention is to provide a microorganism which is capable of reproducible sulfur reduction in carbonaceous material such as coal.

Still another object of the present invention is to provide a microorganism which is capable of reproducible sulfur reduction in coal without the formation of other deleterious or otherwise undesirable by-products.

A further object of this invention is to provide a novel process for the production of a microorganism which is capable of reproducible sulfur reduction in carbonaceous material such as coal.

A still further object of the present invention is to provide a process for the microbial desulfurization of carbonaceous material such as coal.

Another object of this invention is to provide a continuous process for the microbial desulfurization of coal.

Still another object of the present invention is to provide a process for the microbial desulfurization of coal which provides coal having a reduced sulfur content including reduced pyritic sulfur content and particularly reduced organic sulfur content.

These and other objects are achieved herein by providing a viable mixed culture of microorganisms, which have been deposited with the American Type Culture Collection (ATCC) where the culture has been accorded the accession number ATCC 39327, which are capable of reproducible sulfur reduction in coal. These microorganisms are prepared by a process comprising enriching a site of microorganisms with a sulfur containing composition and providing coal and a nutrient medium as a growth substrate for the microorganisms while maintaining essentially neutral pH conditions during the growth of the microorganisms on the coal substrate. Contacting an aqueous coal slurry with the novel microorganism of the present invention provides coal having reduced sulfur content, particularly reduced organic sulfur content.

DETAILED DESCRIPTION OF THE INVENTION

In accordance with the present invention, microorganisms capable of reproducible sulfur metabolism are prepared which can be employed in a continuous process to remove sulfur from coal. The sulfur removed by the process of the present invention includes sulfate, pyrites and particularly organic sulfur. By reproducible sulfur metabolism, is meant, that the microorganisms are capable of sustaining or maintaining effective levels of sulfur metabolism and sulfur reduction in coal from one generation to the next.

Thus, among all the advantages of the present invention, is the ability to remove a substantial amount of organic sulfur from coal.

According to the present invention, a mixed culture of microorganisms identified by ATCC No. 39327 is prepared in situ from normal soil which is enriched with organic sulfur compounds. After an initial period of this environmental pressure selection to provide the microorganisms of the present invention with the capability of organic sulfur metabolism, these microorganisms are grown on a coal substrate in the absence of acid conditions and/or acid producing or acidophilic bacteria such as, for example, Thiobacillus e.g. by maintaining a pH, avoiding acid conditions. Thus, in accordance with the present invention, it has been surprisingly discovered that the novel microorganisms of this invention, ATCC No. 39327 will proliferate and continuously reduce the sulfur content of coal when grown in an environment having an essentially neutral pH.

In more detail, the present invention involves, initially, two critical levels of selectivity in the preparation of a mixed culture of microorganisms which are capable of the reproducible metabolism of organic sulfur.

During a first phase of selectivity, microorganisms are grown in situ in soil which is enriched with organic sulfur compounds. These sulfur containing compounds include cystine, cysteine, methionine, thiophene, thianapthene, beta-mercaptoethanol, methionine sulfoximine, methionine sulfoxide, dibenzothiophene and mixtures thereof and the like. Other ingredients employed during this first phase of selectivity include organic compounds such as biphenyl and the like which are added to the enriched site of microorganisms to induce a phenomena known as cometabolism, i.e., organisms which naturally cleave biphenyl will also cleave dibenzothiophene and thus are environmentally pressure selected for their capability of metabolizing sulfur.

After this initial growth phase characterized by the soil enrichment, the resulting cultures are provided with a growth substrate of coal, preferably in the presence of basal salts and additional organic sulfur compounds and mixtures thereof. Basal salts utilized for this purpose include $CaCl_2$, $MgSO_4$, $NH_4Cl$, $K_2HPO_4$, $KH_2PO_4$ and ferric citrate. These salts may be added as solids or in the form of solutions such as aqueous solutions.

It has been found herein that an essential aspect of the coal substrate growth phase resides in maintaining the pH at essentially neutral levels, preferably between about 6 and about 7, during the entirety of this second phase of growth selection for a time sufficient to provide microorganisms capable of reproducible sulfur metabolism. If this essentially neutral pH level is not maintained, an invariable predominance of acid producing and/or acidophilic bacteria occurs, such as, for example, Thiobacillus which are detrimental to the growth and proliferation of the novel microorganisms of the present invention. Exemplary of this phenomena is the bacterial breakdown of pyrite in the coal, which leads to the production of acid such as $H_2SO_4$ and a consequential drop in pH from roughly neutral values to about 3.0. Such acidic conditions are lethal to many heterotrophic bacteria which exist in soil including, particularly, the mixture or organisms which is the subject matter of this invention.

Several methods may be employed to regulate the pH during this secondary selection growth period. If necessary, conventional buffering techniques, including the addition of buffering agents or neutralizing agents such as NaOH, may be used to adjust to the appropriate pH conditions.

Preferably, the coal employed in the second phase of the growth selection process as well as during the desulfurization process of the present invention has a sufficiently reduced pyrite content, i.e., about 75% reduced from its natural state or thereby containing, for example, between about 1.5 and 3.0% pyrite to avoid the undesirable production of acid. Coal which is substantially free of pyrite is contemplated thereby avoiding the production of acid. However, coal containing natural quantities of pyrite can also be utilized in the process of the present invention which thereby reduces any quantity of pyrite further as well as a significant quantity of the organic sulfur content. As indicated hereinabove, buffering may be required to maintain the pH at proper levels. Moreover, coal employed in the second phase of growth selection as well as the desulfurization process has been beneficiated. A particularly preferred beneficiation process is disclosed, for example, in U.S. Pat. No. 4,304,573, the contents of which are incorporated by reference herein.

A wide variety of coal can be used in the process of the present invention either as the growth substrate of the second phase of growth selection or in the sulfur reduction process itself. Such coals include anthracite, bituminous, subbituminous, mine tailings, fines, lignites and the like. Other finely divided solid carbonaceous materials such as coke may also be employed herein. Furthermore, the coal may be employed herein either in its natural lump state or may be employed in particulate form. Preferably, however, the coal employed herein either as growth substrate or as coal to be subjected to the process of desulfurization is in particulate form.

In another embodiment of the present invention, the mixed culture prepared by the herein identified selection process in accordance with the present invention can be implemented subsequently or concurrently in a batch or continuous process for the organic desulfurization of coal. For example, after proper incubation the mixed culture such as ATCC No. 39327 is inoculated batchwise or continuously into a reaction vessel. Concurrently, an aqueous slurry of particulate coal and a nutrient medium is provided, batchwise or continuously, under continuous stirring and aeration, whereby the coal is subjected to the sulfur reduction activity of the culture mixture, while maintaining the pH under conditions described hereinabove. Sulfur reduced coal and the inhibitory end products of organic metabolism are continuously removed from the reaction vessel. The nutrient medium utilized is selected from the group of organic sulfur compounds and basal salts herein described and additionally from the group of compounds consisting of glucose, succinic acid, butyric acid, and lactic acid and mixtures thereof, the acids being preferred. When these additional compounds are employed, they are generally buffered, such as, for example, by 2 M NaOH, to maintain the requisite pH level hereinbefore discussed. Analysis of the coal treated by this process has been shown to provide an average of about 20% reduction of the total sulfur content of the coal which for the most part is a reduction in the organic sulfur content.

While not wishing to be bound, it is believed that the mixed culture of the present invention, namely, ATCC No. 39327 is comprised of seven aerobic gram negative rods which are probably one or more of the following: Pseudomonas, Acinetobactor, Azotobactor or Flavobacteria. These have been isolated by dilution plating after preparation in accordance with the aforementioned growth process. Other conventional methods of isolating these microorganisms can be employed.

For a better understanding of the present invention together with other and further objects, reference is made to the following description and example.

EXAMPLE

A site for soil enrichment of microorganisms capable of utilizing sulfur, particularly organic sulfur, was selected from the indigenous soil on the grounds at Penn State University and seeded on a weekly basis with a mixture of cysteine, methionine, thiophene, thianapthene and biphenyl. This mixture was designated SM-2.

After an initial growth period of approximately nine months, a soil sample of approximately 20 g was removed, sieved and washed in a buffer solution of 50 mM $K_2HPO_4$, 50 mM $KH_2PO_4$, 50 mM $NH_4Cl$ and 1 mM $MgCl_2.6H_2O$.

The sample was inoculated in Ehrlenmeyer flasks containing SM-2 and basal salts (0.1 g $CaCl_2.H_2O$, 0.1 g $MgSO_4.7H_2O$, 0.002 g ferric citrate in 1000 ml of distilled water, 0.973 g $NH_4Cl$, 0.2 g $K_2HPO_4$ and 0.1 g $KH_2PO_4$ in 200 ml of distilled water). The flasks were incubated for one week at ambient temperature. Cultures recovered from this initial batch culture were inoculated into the reaction vessel of a New Brunswick Bioflo benchtop fermentator.

Figure 1:
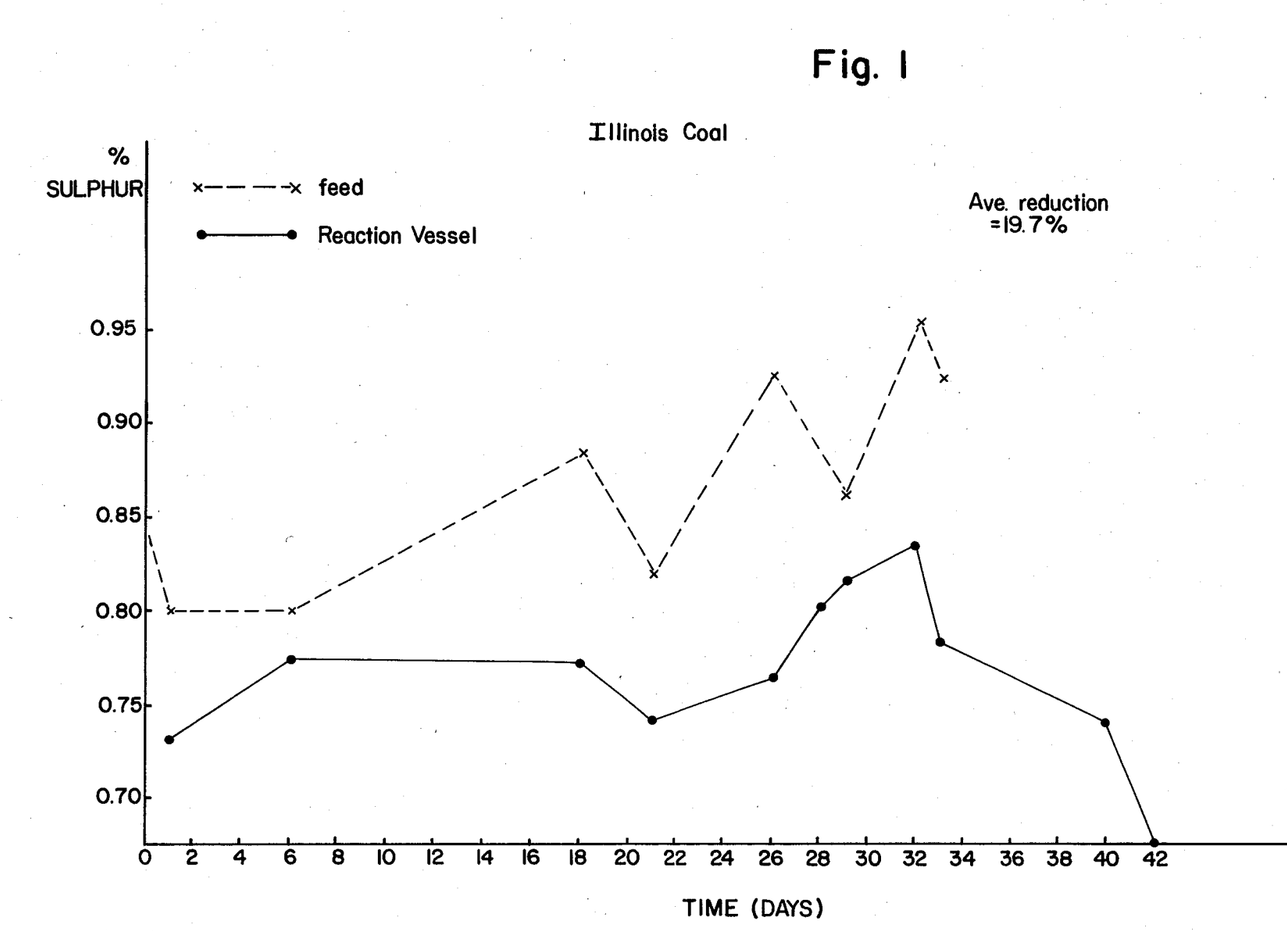
FIG. 1 is a graphic illustration depicting the % sulfur reduction between the feed coal and the end product coal as a result of the microbial desulfurization process of the present invention.
Figure 2:
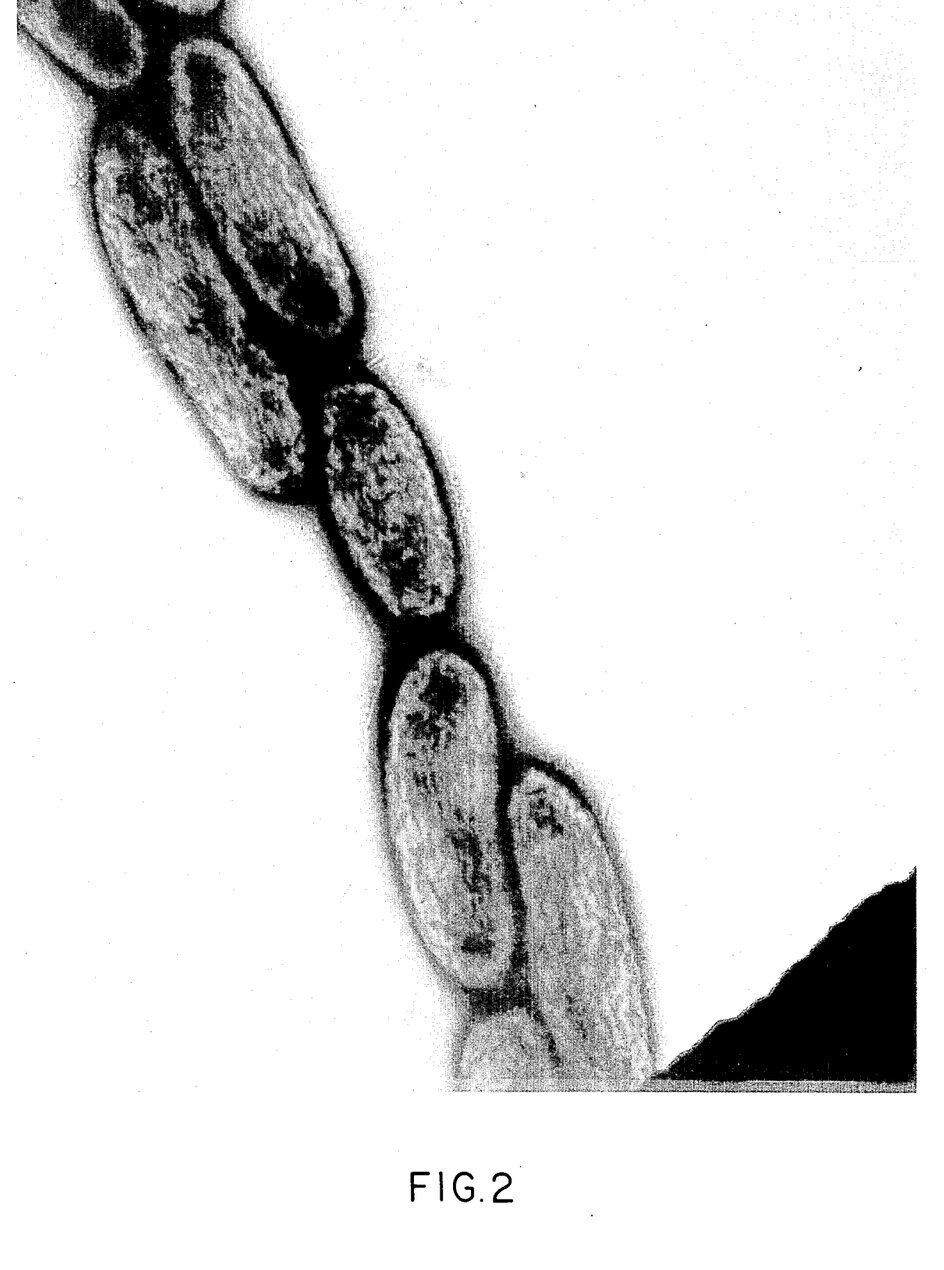
FIGS. 2 through 7 are electron micrographs of six distinct isolates taken from the mixed culture of the present invention assigned ATCC No. 39327.
Figure 3:
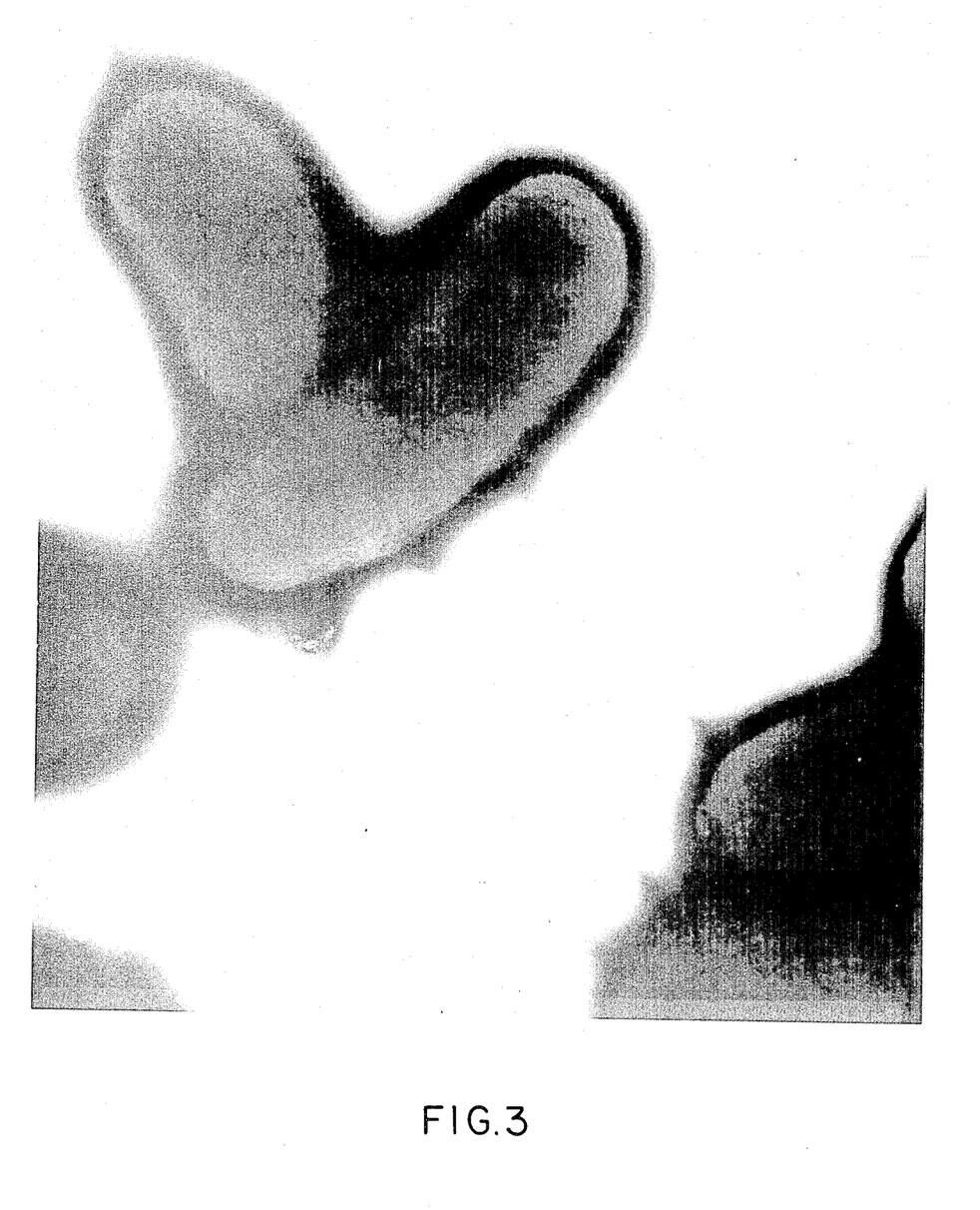
Figure 4:
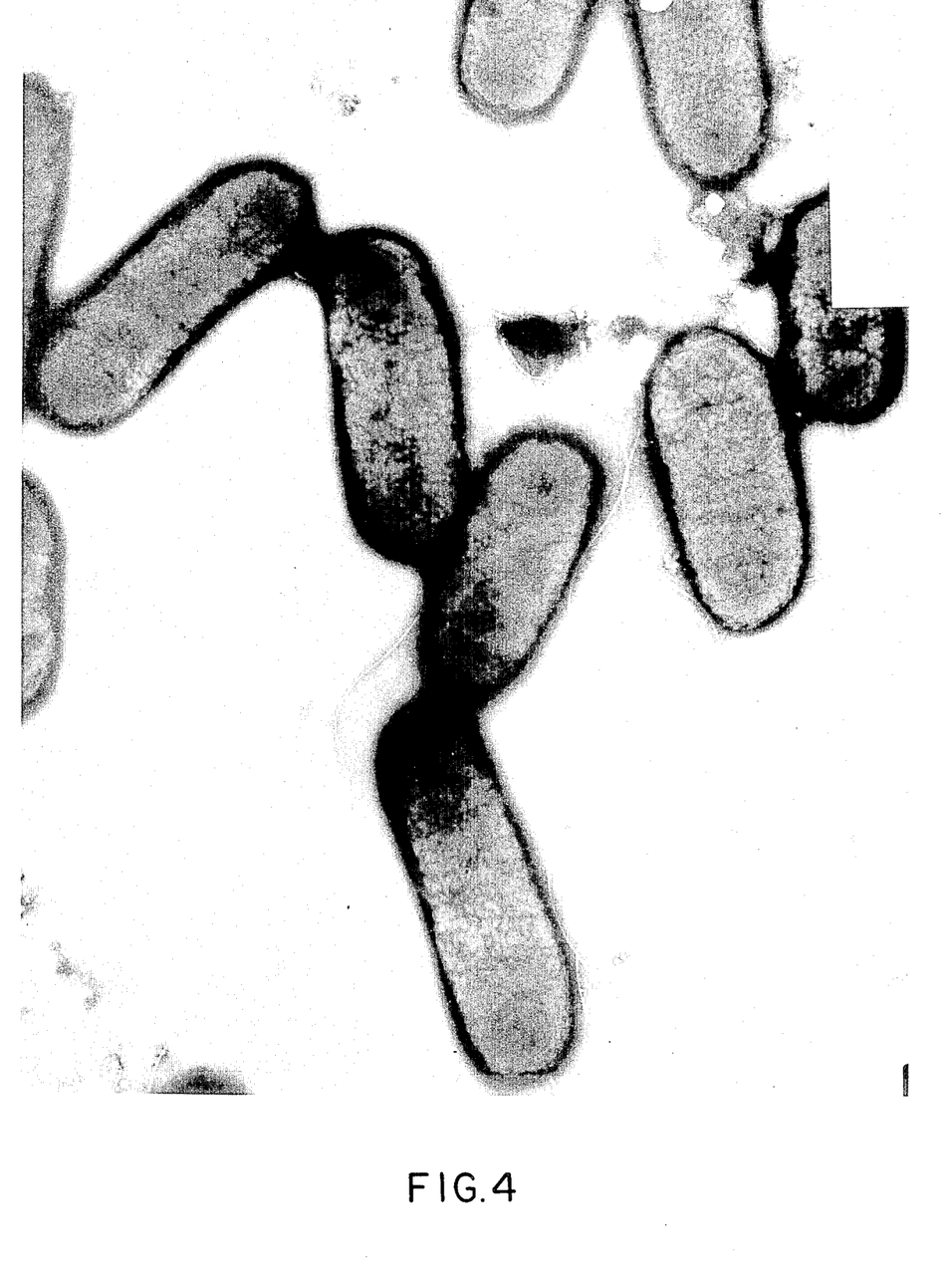
Figure 5:
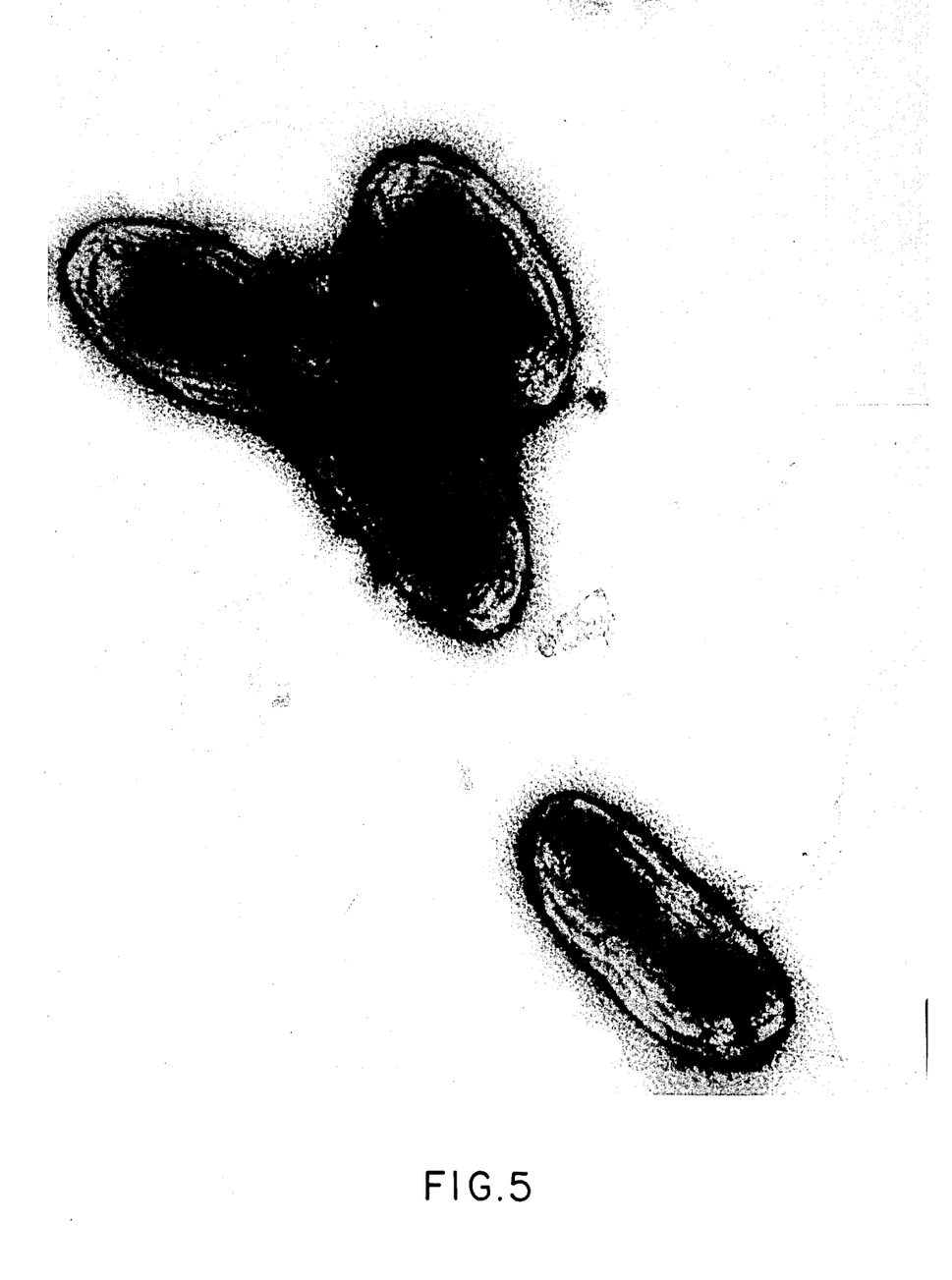
Figure 6:
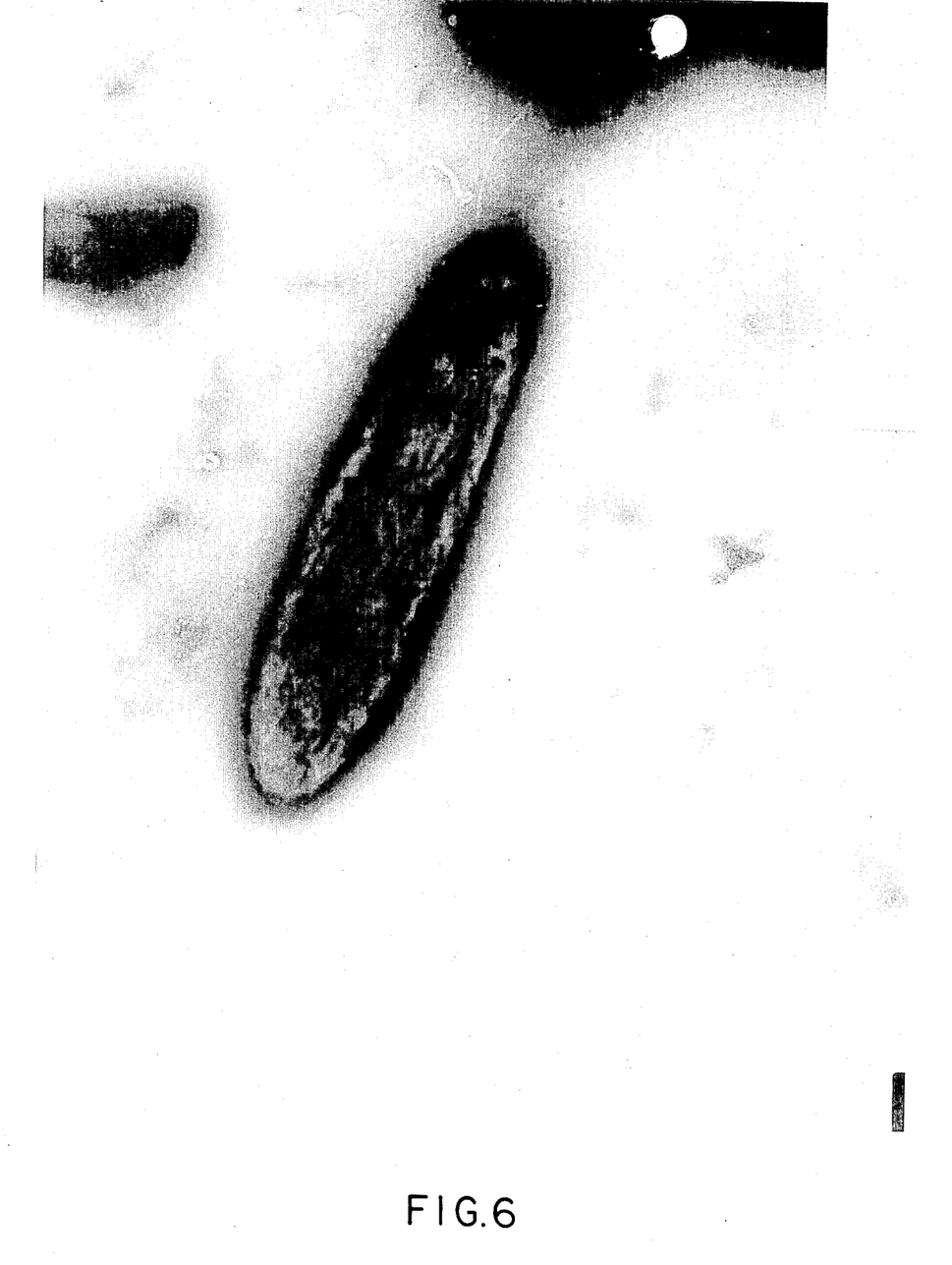
Figure 7:
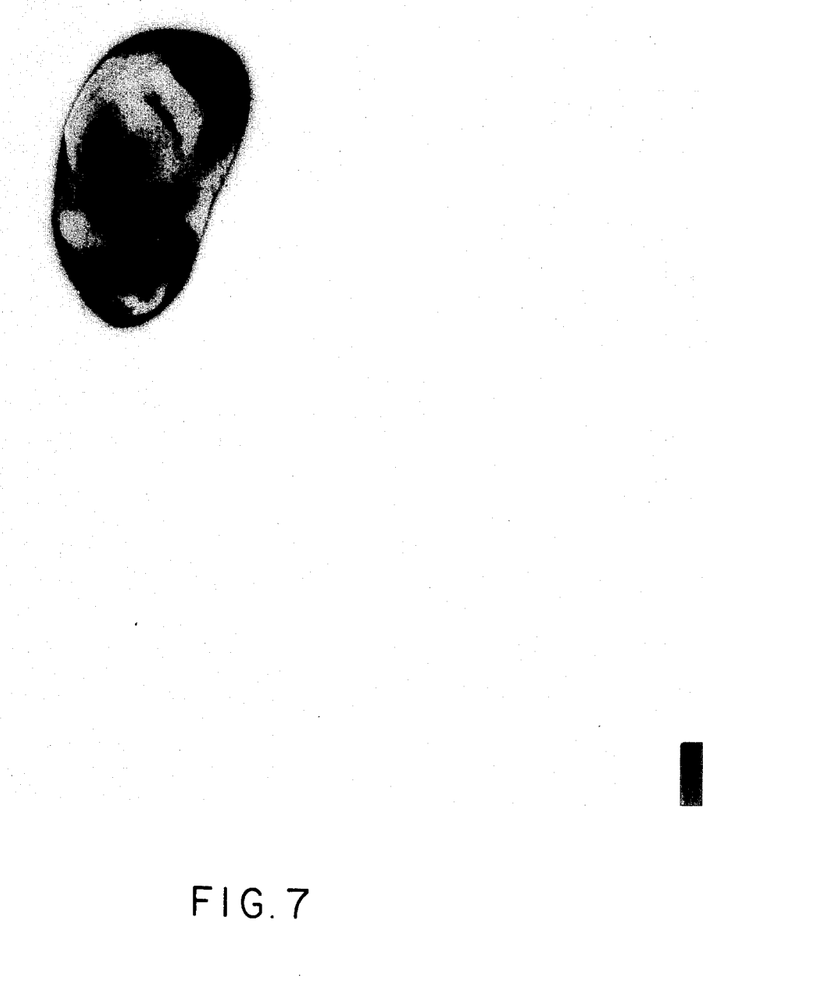

A medium containing Illinois refuse coal, i.e., powdered and beneficiated, succinic acid, lactic acid, butyric acid and sufficient tap water to make 13 liters of solution was introduced into the reaction vessel from an influent reservoir until the reaction vessel contained 750 ml. Flow was shut off and content of the reaction vessel allowed to incubate as a batch culture for about 12 hours. An intermittant flow of 375 ml having a slurry density of about 35 g/liter was initiated each day for the term of the experiment. The reaction vessel was continuously stirred and aerated. If necessary, small additions of sterile NaOH were added to the feed to maintain the pH between about 6 and about 7. Every two or three days during a 43 day term, the sulfur content of the feed coal was compared to the sulfur content of the end product coal. The daily average reduction of sulfur in the coal was determined by a Fisher sulfur analyzer to be 19.7%, the substantial portion being the reduction of the organic sulfur content. The culture mixture showed effective sulfur reduction at ambient temperatures and at neutral values of pH. Seven distinct aerobic gram negative rods have been recognized in the microorganism mixture (ATCC No. 39327). The results are shown graphically in FIG. 1.

Thus, while the invention has been described with reference to certain preferred embodiments, those skilled in the art will realize that changes and modifications may be made thereto without departing from the full and intended scope of the appended claims.

What is claimed is:

1. A process for the selective preparation of a mixed culture of microorganisms, ATCC No. 39327, comprising:
   (a) enriching a site of microorganisms with an organic sulfur containing composition;
   (b) providing coal and a nutrient medium as a growth substrate for the microorganisms produced as a result of step (a) and maintaining an essentially neutral pH during the growth of said microorganisms on said growth substrate for a time sufficient to obtain microorganisms capable of reproducible metabolism of organic sulfur, ATCC No. 39327.

2. The process of claim 1 which further comprises recovering the microorganisms capable of reproducible sulfur metabolism resulting from step (b).

3. The process of claim 1 wherein said organic sulfur containing composition comprises a sulfur compound selected from the group consisting of cystine, cysteine, methionine, thiophene, thianapthene, beta-mercaptoethanol, methionine sulfoximine, methionine sulfoxide, dibenzothiophene and mixtures thereof.

4. The process of claim 1 which further comprises enriching the microorganism site with biphenyl.

5. The process of claim 1 wherein the essentially neutral pH is maintained by the addition of buffering agents.

6. The process of claim 1 wherein the essentially neutral pH of the growth substrate is maintained by avoiding the presence of acid on the growth substrate.

7. The process of claim 1 wherein the essentially neutral pH of the growth substrate is maintained by avoiding growth of acid producing and acidophilic bacteria on the growth substrate.

8. The process of claim 1 wherein the coal is substantially free of pyrite thereby avoiding the production of acid.

9. The process of claim 1 wherein the coal is beneficiated.

10. The process of claim 1 wherein the pH is maintained between about 6 and about 7.

11. The process of claim 1 wherein the nutrient medium is selected from the group consisting of organic sulfur compounds, basal salts and mixtures thereof.

12. The process of claim 11 wherein the sulfur compound of the nutrient medium is selected from the group consisting of cystine, cysteine, methionine, thiophene, thianapthene, beta-mercaptoethanol, methionine sulfoximine, methionine sulfoxide, dibenzothiophene and mixtures thereof.

13. The process of claim 11 wherein the basal salt is selected from the group consisting of $CaCl_2$, $MgSO_4$, $NH_4Cl$, $K_2HPO_4$, $KH_2PO_4$, ferric citrate and mixtures thereof.

14. The process of claim 1 wherein the nutrient medium further comprises a compound selected from the group consisting of glucose, butyric acid, succinic acid, lactic acid and mixtures thereof.

15. The process of claim 1 wherein the growth substrate and microorganisms are provided continuously.

16. The mixed culture of microorganisms consisting of ATCC No. 39327.

17. A process for the microbial desulfurization of coal comprising:
   contacting an aqueous coal slurry with ATCC No. 39327 in the presence of a nutrient medium.

18. The process of claim 17 wherein the nutrient medium is selected from the group consisting of cystine, cysteine, methionine, thiophene, thianapthene, beta-mercaptoethanol, methionine sulfoximine, methionine sulfoxide, dibenzothiophene, glucose, butyric acid, succinic acid, lactic acid, $CaCl_2$, $MgSO_4$, $NH_4Cl$, $K_2HPO_4$, $KH_2PO_4$, ferric citrate and mixtures thereof.

19. The process of claim 17 wherein the pH is maintained between about 6 and 7.

20. The process of claim 17 wherein the temperature is maintained at about room temperature.

* * * * *